US00PP26657P2

(12) United States Plant Patent
Irie

(10) Patent No.: US PP26,657 P2
(45) Date of Patent: Apr. 26, 2016

(54) ***HYDRANGEA* PLANT NAMED 'H2002'**

(50) Latin Name: *Hydrangea macrophylla*
Varietal Denomination: H2002

(71) Applicant: Ryoji Irie, Kyoto (JP)

(72) Inventor: Ryoji Irie, Kyoto (JP)

( * ) Notice: Subject to any disclaimer, the term of this patent is extended or adjusted under 35 U.S.C. 154(b) by 17 days.

(21) Appl. No.: 14/120,513

(22) Filed: May 28, 2014

(51) Int. Cl.
*A01H 5/02* (2006.01)

(52) U.S. Cl.
USPC ..... Plt./250

(58) Field of Classification Search
USPC ..... Plt./250
CPC ..... A01H 5/02; A01H 5/00
See application file for complete search history.

(56) References Cited

PUBLICATIONS http://blog.thompson-morgan.com/hydrangea-miss-saori-rhs-chelsea-flower-show-plant-of-the-year-2014/; May 23, 2014; 4 pages.*

* cited by examiner

*Primary Examiner* — Kent L Bell
(74) *Attorney, Agent, or Firm* — Penny J. Aguirre

(57) ABSTRACT

A new cultivar of *Hydrangea macrophylla* named 'H2002' that is characterized by its double sterile flowers with sepals that are light yellow-green to white with red margins, its free flowering and repeating blooming habit, its rounded mop-head type inflorescences, its young foliage that is tinged with greyed-red, and its lack of fertile flowers.

2 Drawing Sheets

Genus/species: *Hydrangea macrophylla.*
Varietal denomination: 'H2002'.

CROSS REFERENCE TO RELATED APPLICATIONS

This application is related to U.S. Plant Patent Applications filed for plants derived from similar parentage in the Inventor's breeding program that are entitled *Hydrangea* Plant Named 'PERFECTION' (U.S. Plant Pat. No. 22,221), *Hydrangea* Plant Named 'FREEDOM' (U.S. Plant Pat. No. 22,210), and 'RIE 05' (U.S. Plant Pat. No. 18,508).

BACKGROUND OF THE INVENTION

The present invention relates to a new and distinct cultivar of *Hydrangea macrophylla* and will be referred to hereafter by its cultivar name, 'H2002'. 'H2002' represents a new bigleaf *hydrangea*, a perennial shrub grown for landscape use.

'H2002' was derived from an ongoing controlled breeding program by the Inventor that focuses on developing new cultivars of bigleaf *hydrangeas* with unique flower colors and double flowers. 'H2002' originated from a cross conducted in the Inventor's trial garden in 2002 in Kyoto, Japan between an unnamed plant of *Hydrangea macrophylla* from the Inventor's breeding collection as the female parent and *Hydrangea macrophylla* 'Yamaajisai' (not patented) as the male parent. The new *Hydrangea* was selected as a unique single plant from the progeny of the cross in 2006.

Asexual propagation of the new cultivar was first accomplished by softwood stem cuttings in Kyoto, Japan in 2008 by the Inventor. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'H2002' as a unique cultivar of *Hydrangea macrophylla.*

1. 'H2002' exhibits double sterile flowers with sepals that are light yellow-green to white with red margins.
2. 'H2002' exhibits a free flowering and repeating blooming habit.
3. 'H2002' exhibits rounded mop-head type inflorescences.
4. 'H2002' exhibits young foliage that is tinged with greyed-red.
5. 'H2002' lacks fertile flowers.

'Yamaajisai', the male parent of 'H2002' differs from 'H2002' in having smaller flowers that are pink in color, in having more flat shaped inflorescences, weaker stems, and in having green young foliage. The seeds were pooled from various female plants and therefore the exact characteristics of the female parent are unknown. 'H2002' can be most closely compared to the cultivars 'FREEDOM', 'PERFECTION' and 'RIE 05. 'FREEDOM' differs from 'H2002' in having whitish to light pink sterile flowers with red markings in the center. 'PERFECTION' differs from 'H2002' in having inflorescences with sterile flowers that are dark pink in color and less round in shape. 'RIE 05' differs from 'H2002' in having sterile flowers that are pink in color and in having young foliage that is green in color.

BRIEF DESCRIPTION OF THE DRAWINGS

The photographs in the figures were taken of an 18 month-old plant of 'H2002' as grown in an unheated greenhouse with ambient light in a 1.5-liter container in De Kwakel, The Netherlands.

The photograph in FIG. 1 provides side view of 'H2002' in full bloom and a view of the young foliage.

Figure 1:
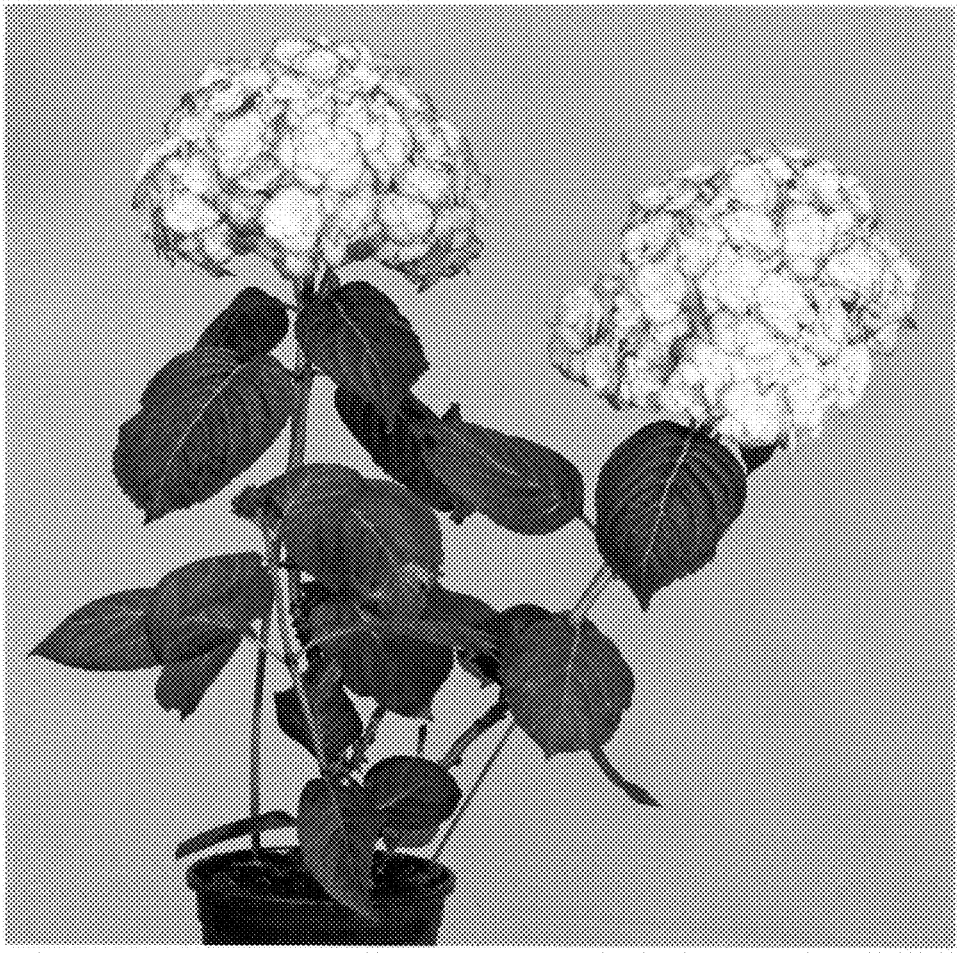
Figure 2:
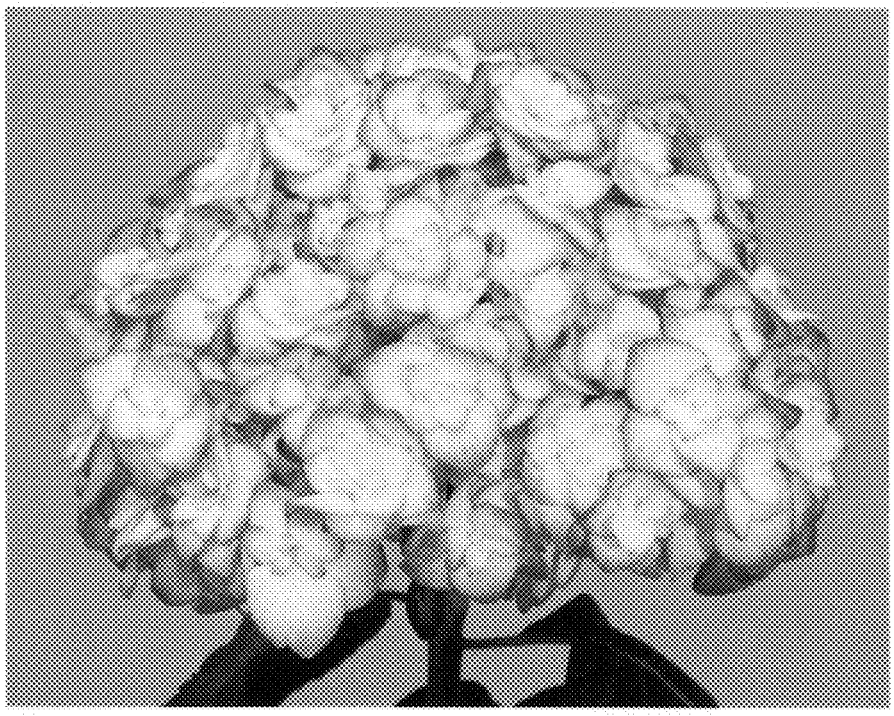

The photograph in FIG. 2 provides a close-up view of an inflorescence of 'H2002'.

Figure 3:
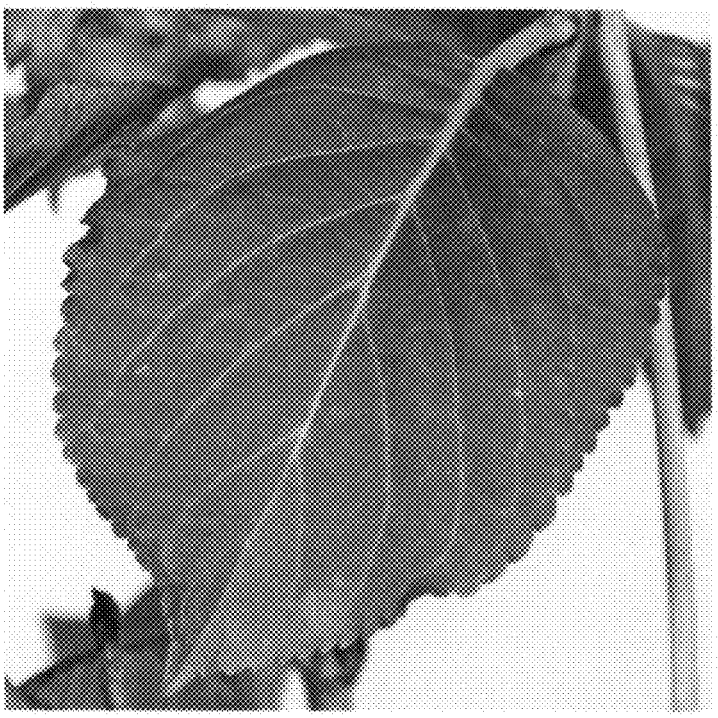

The photograph in FIG. 3 provides a close-up view of a mature leaf of 'H2002'.

The colors in the photographs are as close as possible with the digital photography and printing techniques utilized and the color codes in the detailed botanical description accurately describe the new *Hydrangea*.

BOTANICAL DESCRIPTION OF THE PLANT

The following is a detailed description of 18 month-old plants of the new cultivar as grown in an unheated greenhouse in 1.5-liter containers in a greenhouse in De Kwakel, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Repeat blooming habit from early June through October in The Netherlands.

*Plant habit*.—Broadly upright, overall globular in shape, inverted triangular.

*Height and spread*.—Average of 45.7 cm in height and 45.9 cm in diameter.

*Hardiness*.—At least in U.S.D.A. Zones 4 to 9.

*Diseases resistance*.—Not more susceptible or resistant to pests and diseases than other *Hydrangea macrophylla* cultivars.

*Root description*.—Fibrous, dense.

*Plant vigor*.—Moderate to high.

*Propagation*.—Softwood stem cuttings.

*Growth rate and vigor*.—Moderate to high.

Stem description:

*Stem shape*.—Round.

*Stem strength*.—Moderately strong.

*Stem aspect*.—Upright to an average angle of 60°.

*Stem color*.—Immature stem; 144B to 144C, mature stem; a blend of 166B and 200D.

*Stem size*.—Average of 28.1 cm (excluding the inflorescence) in length and 6 mm in diameter.

*Stem surface*.—Smooth, moderately covered with narrow oblong lenticels; an average of 1.5 mm in length and 0.5 mm in width, N186C in color.

*Branching*.—Moderately freely branching, including basal branching, with an average of 4 lateral branches, branching improves with pinching.

*Internode length*.—Average of 5.1 cm.

Foliage description:

*Leaf shape*.—Broad ovate to ovate.

*Leaf arrangement*.—Opposite.

*Leaf division*.—Simple.

*Leaf number*.—Average of 6 (3 pairs) per lateral branch.

*Leaf base*.—Very short attenuate to obtuse.

*Leaf apex*.—Short apiculate.

*Leaf margins*.—Serrate.

*Leaf venation*.—Pinnate, upper surface; 145A in color, lower surface; 145A to 145B in color.

*Leaf size*.—Average of 11.8 cm in length and 8.9 cm in width.

*Leaf attachment*.—Petiolate.

*Leaf surface*.—Upper surface; slightly glossy and slightly rugose, lower surface matte.

*Leaf color*.—Immature upper surface; 137B and moderately to strongly tinged with 166A, immature lower surface; 146B and tinged 181A to 181B, mature upper surface; a color between 139A and 147A, mature lower surface; 147B and tinged with 178A to 178B.

*Peduncles*.—Average of 6 cm in length and 3.5 mm in diameter, ranging 40° angle to vertical, strong, 145A in color, glabrous surface.

*Petioles*.—Average of 2.2 cm in length and 3 mm in diameter, upper and lower surface 145A in color, both surfaces are smooth and slightly glossy.

Inflorescence description:

*Inflorescence type*.—Globular, mophead, compound corymb of double sterile flowers, no fertile flowers present.

*Lastingness of inflorescence*.—Persistent with color lasting up to 3 weeks.

*Inflorescence number*.—One per lateral or sublateral stem.

*Inflorescence size*.—Average of 17.3 cm in height and 18.7 cm in diameter.

*Flower number*.—An average of 350 sterile flowers. .

*Flower fragrance*.—None.

*Flower aspect*.—Upright and outward.

*Flower type*.—Double, rotate.

*Flower size*.—An average of 4.1 cm in diameter and 1.4 cm in depth.

*Flower buds*.—An average of 7 mm in length and 8 mm in width, obcordate in shape, 145A, tip is 183A to 183B.

*Peduncles*.—Not present.

*Pedicels*.—Up to 3.8 cm in length and 2 mm in diameter, held at an average angle of 45° to vertical, 75D in color, moderate strength, dull and moderately covered with very short small hairs; an average length of 0.3 mm and N155D in color.

*Petals*.—Not present.

*Sepals*.—Average of 15, rotate in arrangement, both surfaces smooth and dull, broad obovate in shape, margin is irregular serrate to entire, tip obtuse, base broad and bluntly acute, an average of 2 cm in length and 1.7 cm in width, color: upper surface color when opening; 150D and 155A with margins 53A to 53C, lower surface color when opening; 150D with margins 185C to 185D, upper surface when fully open; NN155C with margins 63A to 63B, lower surface when fully open; NN155C with margins a color between 63C and 185D, fading; upper surface fading to NN155C with margins 63B to 63C, lower surface fading to NN155C with margins a color between 63C and 185D.

Reproductive organs:

*Androecium*.—Not present.

*Gynoecium*.—Sterile flowers; average of 2 rudimentary pistils present in 20% of the sterile flowers, 2 mm in length, stigma is club-shaped and 187C to 187D in color, style is about 1.7 mm in length and 150D in color, ovary is not present, fertile flowers were not formed.

*Fruit and seed*.—No seeds or fruit are formed as there are no fertile flowers formed.

It is claimed:

1. A new and distinct cultivar of *Hydrangea* plant named 'H2002' substantially as herein illustrated and described.

* * * * *